United States Patent [19]
Kaplan et al.

[11] 3,941,809

[45] Mar. 2, 1976

[54] TECHNIQUE FOR PREPARATION OF FULVALENES

[75] Inventors: Martin Louis Kaplan, Whippany; Fred Wudl, Chester, both of N.J.

[73] Assignee: Bell Telephone Laboratories, Incorporated, Murray Hill, N.J.

[22] Filed: Jan. 20, 1975

[21] Appl. No.: 542,246

[52] U.S. Cl. ............................................. 260/327 M
[51] Int. Cl.$^2$ ........................................ C07D 339/06
[58] Field of Search .................... 260/327 M, 239 R

[56] References Cited
OTHER PUBLICATIONS

Solid State Communications, Vol. 14, 1974.

J. of the Am. Chem. Soc., Jan. 26, 1972.

*Primary Examiner*—Henry R. Jiles
*Assistant Examiner*—C. M. S. Jaisle
*Attorney, Agent, or Firm*—E. M. Fink

[57] ABSTRACT

A technique for preparing a wide range of fulvalenes by a reductive procedure is described. The procedure involves reducing an organic halide to its corresponding partially hydrogenated derivative which is reacted with fluoboric acid to yield a fluoborate. Deprotonation of the fluoborate yields the desired compound. The described technique maximizes the yield and quality of fulvalenes produced and permits the preparation of thia, selena and tellura fulvalenes.

4 Claims, No Drawings

TECHNIQUE FOR PREPARATION OF FULVALENES

This invention relates to a technique for the preparation of fulvalenes. More particularly, the present invention relates to a reductive procedure for synthesizing fulvalenes from ditholium iodides.

Recently, there has been a birth of interest in a compound commonly known as 1,4,5,8-tetrahydro-1,4,5,8-tetrathiafulvalene of the general formula

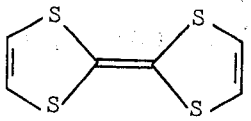

This compound and its derivatives have been found to form stable radical cations which evidence high d-c conductivity, so suggesting their use in semiconductive devices and as solid state organic conductors.

Heretofore, tetrathiafulvalenes have been prepared by a complex oxidative procedure involving the formation of 1,3-dithiole-2-thione from acetylene, sulfur and carbon disulfide and subsequent oxidation of the thione to 1,3-ditholium hydrogen sulfate and coupling of the salt with an appropriate base. Although fulvalenes prepared in the foregoing manner have been found satisfactory, limitations upon yield and quality coupled with practical limitations of oxidative techniques have prompted a search for suitable alternates.

In accordance with the present invention, this end is attained by means of a novel synthesis technique which relies upon the use of reductive agents to maximize the variety of compounds produced. The yield of fulvalenes are not only superior to those attained in accordance with prior art processes but the procedure also permits the preparation of various fulvalene derivatives.

The first step in the preparation of fulvalene derivatives in accordance with the present invention involves reducing (in the presence of any polar solvent) an organic halide of the general formula

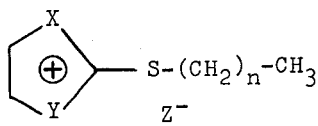

wherein X is selected from the group consisting of sulfur, selenium and tellurium and y is selected from the group consisting of sulfur and selenium, $n$ is an integer from 0-4, and Z is a halogen atom to yield the corresponding partially hydrogenated compound in accordance with Equation (1) below:

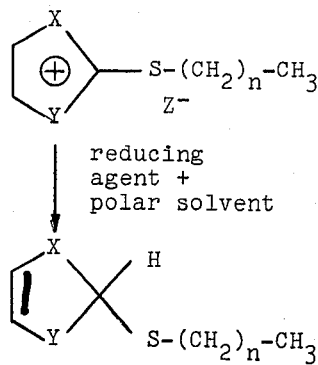

Reducing agents suitable for use in effecting the foregoing reaction are selected from among the metal borohydrides, the alkali and alkaline earth metal borohydrides being particularly well suited for this purpose. Sodium borohydride ($NaBh_4$) and sodium cyano borohydride ($NaBH_3CN$) have proven most effective for this purpose.

The reduction must be effected at temperatures less than 15°C due to the exothermic nature of the reaction, a large excess of the borohydride, well beyond stoichiometry, being employed.

Following, the partially hydrogenated derivative so obtained is reacted with anhydrous fluoboric acid in stoichiometric amounts or amounts slightly beyond stoichiometry to yield the fluoborate derivative shown in Equation (2) below:

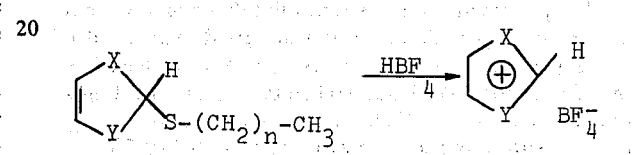

Upon deprotonation with an excess of any alkyl tertiary amine, the resultant fluoborate yields the desired fulvalene in accordance with Equation (3):

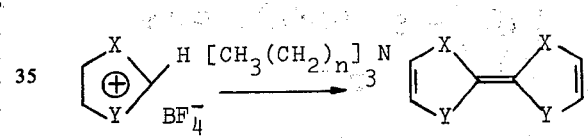

wherein $n$ is an integer from 0-4.

An example of the present invention is set forth below. It will be understood by those skilled in the art that the example is set forth merely for the purpose of exposition and is not restrictive in nature.

EXAMPLE

Into a 2-liter Erlenmeyer flask containing a magnetic stirrer was placed 50.0 grams (0.18 moles) of 2-thiomethyl-1,3-ditholium oidide and 500 milliliters of methanol. The mixture was stirred and cooled in an ice bath. While preventing the temperature from rising above 15°C, 34.5 grams (0.93 moles) of sodium borohydride were continuously added in small quantities. After completing the addition, stirring was continued for 3 hours and 1 liter of anhydrous ether was then added to precipitate the sodium iodide which had formed. The resultant solution was stored at −15°C overnight and then decanted into a 2-liter separatory funnel, washed three times with water (200 milliliters each time), dried over magnesium sulfate, filtered and concentrated on a rotary evaporator.

The resultant 2-S-methyl-1,3-dithiole was an orange-yellow oil and evidenced an inner spectrum in $CdCl_3$ which consisted of three singlets at $\tau$ 7.85, 4.03 and 3.93. The ratio of the areas of low field lines to high field lines was approximately 1:1.

To the stirred, cooled (0°) solution of 2-S-methyl-1,3-dithiole in 100 milliliters of acetic anhydride in a 500 milliliter Erlenmeyer flask was added dropwise 33.3 grams (0.18 moles) of a 48% fluoboric acid solution in acetic anhydride. After completion of the addition, approximately 200 milliliters of anhydrous ether was added. The resultant white 1,3-dithiolium fluoborate salt was collected in a Buchner funnel and washed with anhydrous ether, The nmr of the salt consisted of a doublet at $\tau$ 0.33 (J) = 2 Hz and a triplet at $\tau$ 1.65 (J) = 2 Hz.

The 1,3-dithiolium fluoborate (28 grams obtained previously) was dissolved in 100 milliliters of acetonitrite in a 500 milliliter Erlenmeyer flask. The solution was magnetically stirred, at 0°C and triethylamine was added (approximately 50 ml) until the formation of yellow crystals was observed. An additional 10 milliliters of triethylamine was added and stirring continued for 10 minutes. Water was next added to precipitate the product. The resultant yellow-orange crystals of 1,4,5,8-tetrahydro-1,4,5,8-tetrathiafulvalene were collected, washed with water and air dried. The yield of crude product was 15.0 grams (100% yield based on the fluoroborate). Recrystallization from cyclohexane/hexane (500 mil/300 ml) resulted in yellow-orange needles with a melting point from 119.1°–119.3°C.

What is claimed is:

1. Method for the preparation of a fulvalene which comprises the steps of
   a. reducing an organic halide of the general formula

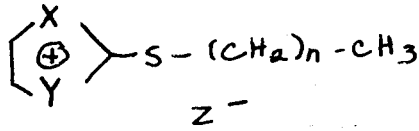

with a reducing agent selected from the alkali and alkaline earth metal borohydrides at a temperature less than 15°C. wherein X is selected from the group consisting of sulfur, selenium and tellurium, Y is selected from the group consisting of sulfur and selenium, n is an integer from 0–4 and Z if a halogen atom, so resulting in the formation of the corresponding partially hydrogenated compound

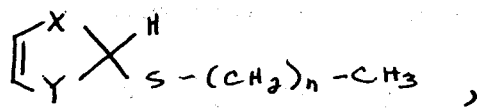

b. reacting the partially hydrogenated derivative with fluorboric acid to yield the corresponding fluoborate derivative, and
   c. deprotonating the fluoborate derivative with an alkyl tertiary amine to yield the fulvalene.

2. Method in accordance with claim 1 wherein the alkyl tertiary amine is of the general formula [CH$_3$(CH$_2$)$_n$]$_3$ N wherein $n$ is an integer from 0–4.

3. Method in accordance with claim 1 wherein the fulvalene is 1,4,5,8-tetrahydro-1,4,5,8-tetrathiafulvalene.

4. Method in accordance with claim 3 wherein the fulvalene is prepared by reducing 2-thiomethyl-1,3-ditholium iodide with sodium borohydride to yield 2-S-methyl-1,3-dithiole, reacting the dithiole with fluoboric acid to yield 1,3-dithiolium fluoborate, and deprotonating the fluoborate with triethylamine to yield the fulvalene.

* * * * *